US009061036B2

(12) United States Patent
Yan et al.

(10) Patent No.: US 9,061,036 B2
(45) Date of Patent: Jun. 23, 2015

(54) ORAL LIQUID FOR TREATING ALLERGIC COUGH

(71) Applicants: Yiwen Yan, Guangzhou (CN); Haocheng Yan, Guangzhou (CN); Zongguo Ye, Guangdong (CN)

(72) Inventors: Yiwen Yan, Guangzhou (CN); Haocheng Yan, Guangzhou (CN); Zongguo Ye, Guangdong (CN)

( * ) Notice: Subject to any disclaimer, the term of this patent is extended or adjusted under 35 U.S.C. 154(b) by 0 days.

(21) Appl. No.: 14/349,699

(22) PCT Filed: Dec. 25, 2012

(86) PCT No.: PCT/CN2012/087366
§ 371 (c)(1),
(2) Date: Apr. 4, 2014

(87) PCT Pub. No.: WO2013/102410
PCT Pub. Date: Jul. 11, 2013

(65) Prior Publication Data
US 2014/0322347 A1    Oct. 30, 2014

(30) Foreign Application Priority Data

Jan. 5, 2012  (CN) .......................... 2012 1 0003475

(51) Int. Cl.

| | | |
|---|---|---|
| *A01N 65/00* | (2009.01) | |
| *A61K 35/64* | (2015.01) | |
| *A61K 36/00* | (2006.01) | |
| *A61K 36/535* | (2006.01) | |
| *A61K 9/00* | (2006.01) | |
| *A61K 35/62* | (2006.01) | |
| *A61K 36/752* | (2006.01) | |
| *A61K 36/8966* | (2006.01) | |
| *A61K 36/899* | (2006.01) | |
| *A61K 36/904* | (2006.01) | |
| *A61K 36/23* | (2006.01) | |
| *A61K 36/28* | (2006.01) | |

(52) U.S. Cl.
CPC ............... *A61K 35/642* (2013.01); *A61K 36/00* (2013.01); *A61K 36/752* (2013.01); *A61K 36/8966* (2013.01); *A61K 36/899* (2013.01); *A61K 36/904* (2013.01); *A61K 36/23* (2013.01); *A61K 36/28* (2013.01); *A61K 36/535* (2013.01); *A61K 9/0053* (2013.01); *A61K 35/62* (2013.01); *A61K 35/64* (2013.01)

(58) Field of Classification Search
CPC ....................................................... A61K 36/00
USPC ........................................................ 424/725
See application file for complete search history.

(56) References Cited

FOREIGN PATENT DOCUMENTS

| | | | |
|---|---|---|---|
| CN | 1605349 | A | 4/2005 |
| CN | 101229319 | A | 7/2008 |
| CN | 101229338 | A | 7/2008 |
| CN | 102512495 | A | 6/2012 |

OTHER PUBLICATIONS

PCT/CN2012/087366—International File Date: Dec. 25, 2012—International Search Report; 3 pgs.
Chen, Jianwen, Chansusan Zhi Liao Holi Yuan Xing Ke Sou 65 Li, Mordern Journal of Integrated Traditional Chinese and Western Medicine, vol. 12, No. 5, Mar. 2003; pp. 492 and 493.

*Primary Examiner* — Michael Meller
(74) *Attorney, Agent, or Firm* — Schmeiser, Olsen & Watts, LLP

(57) ABSTRACT

A medicine for treating allergic cough comprises 5 to 25 parts by weight of *Perilla* Leaf, 5 to 25 parts by weight of Periostracum Cicada, and 5 to 25 parts by weight of *lumbricus*. The medicine is in the form of concentrated decoction, tablet, pill, granule or capsule. The medicine has effects of dispelling wind-cold, dispelling wind-heat, relieving cough and preventing asthma. The medicine provides excellent anti-allergic effect and can be used for treating allergic cough.

5 Claims, No Drawings

ORAL LIQUID FOR TREATING ALLERGIC COUGH

FIELD OF TECHNOLOGY

The present invention relates to the field of Chinese medicine, particularly to an oral liquid for treating allergic cough.

BACKGROUND

Cough is a cardinal symptom of lung diseases. Whatever exogenous or endogenous, cough may occur in any person whose lung qi is deficiency in diffusion and purification. To treat cough, ways of relieving cough, eliminating phlegm, preventing asthma, anti-inflammation, etc., are usually applied. Chinese medicine has been used to treat cough for centuries. Researches have shown that some kinds of Chinese medicine are capable of moistening lung, resolving masses, relieving cough, and eliminating phlegm.

The so-called anemogenous cough in the field of Chinese medicine refers to that lung would firstly be invaded by external pathogen, causing a lung qi blockage and deficiency in convergence, when catching the external pathogen occasionally. Then liver qi would ascend, leading to rising of the lung qi instead of falling, thereby cough appears, which is called allergic cough in field of Western medicine. The clinical features of such cough are the chronic cough lasting longer than two month without reasons, which is the paroxysmal allergic dry cough accompanying with phlegm of white bubble type; The symptom would be more serious after inhaling smoke or chemical smell such as paint, DDVP, etc.

Currently it is rare to find Chinese patent medicines for treating allergic cough, and the curative effects are being expected to be improved.

SUMMARY

An aspect relates to an oral liquid for treating allergic cough, which is effective in anti-inflammation, relieving cough, and preventing asthma. It works well in clinical treatment.

An aspect relates to an oral liquid for treating allergic cough, comprising 5 to 25 parts by weight of *Perilla* Leaf, 5 to 25 parts by weight of Periostracum Cicada, and 5 to 25 parts by weight of *lumbricus*. The oral liquid is a concentrated decotion.

The prescription further comprises 5 to 25 parts by weight of Radix *Peucedani*, 5 to 25 parts by weight of Radix *Stemonae*, 5 to 25 parts by weight of *phragmites* stem, 5 to 25 parts by weight of *Flos Farfarae*, 5 to 25 parts by weight of *Bulbus Fritillariae Cirrhosae*, and 5 to 25 parts by weight of *Exocarpium Citri Rubrum*.

The oral liquid for treating allergic cough mentioned above is used for preparing medicine for treating allergic cough.

A pharmaceutical preparation for treating allergic cough, comprising 5 to 25 parts by weight of *Perilla* Leaf, 5 to 25 parts by weight of Periostracum Cicada, and 5 to 25 parts by weight of *lumbricus*. The pharmaceutical preparation is in the form of tablets, pills, granules or capsules.

In the present invention, *Perilla* Leaf, Periostracum Cicada, and *lumbricus* are formed into a dominated medicine, having the effect of anti-allergy, eliminating wind and cold, dispersing wind and heat, relieving cough, and preventing asthma. They work well in clinical treatment. Further, the effect would be better together with other suitable components.

DETAILED DESCRIPTION

The present invention relates an oral liquid for treating allergic cough, comprising 5 to 25 parts by weight of *Perilla* Leaf, 5 to 25 parts by weight of Periostracum Cicada, and 5 to 25 parts by weight of *lumbricus*. The oral liquid is a concentrated decoction. Preferably, the prescription further comprise 5 to 25 parts by weight of Radix *Peucedani*, 5 to 25 parts by weight of Radix *Stemonae*, 5 to 25 parts by weight of *Phragmites* stem, 5 to 25 parts by weight of *Flos Farfarae*, 5 to 25 parts by weight of *Bulbus Fritillariae Cirrhosae*, and 5 to 25 parts by weight of *Exocarpium Citri Rubrum*, which would contribute to a good effect together with the dominated medicine.

More preferably, the prescription comprises 10 to 20 parts by weight of *Perilla* Leaf, 10 to 20 parts by weight of Periostracum Cicada, 10 to 20 parts by weight of *lumbricus*, 10 to 20 parts by weight of Radix *Peucedani*, 10 to 20 parts by weight of Radix *Stemonae*, 10 to 20 parts by weight of *phragmites* stem, 10 to 20 parts by weight of *Flos Farfarae*, 10 to 20 parts by weight of *Bulbus Fritillariae Cirrhosae*, and 10 to 20 parts by weight of *Exocarpium Citri Rubrum*.

The oral liquid is prepared by concentrating and decocting the components above. Chinese patent medicines in different dosage forms, such as tablets, pills, granules or capsules, etc., can be prepared by ordinary pharmaceutical preparation technology for requirements of different people.

In the prescription, the effects of components are as follows:

*Perilla* Leaf: warm-natured, in pungent flavor, effective in dispelling wind-cold, promoting qi circulation to alleviate middle energizer, detoxification and anti-allergy;

*Lumbricus*: cold-natured, in salty flavor, effective in clearing heat and extinguishing wind, preventing asthma, and dredging collaterals;

Periostracum Cicada: in sweet-bitter flavor, effective in dispersing wind-heat, promoting eruption and extinguishing wind, diffusing lung qi, and dispersing wind and relieving itching;

Radix *Stemonae*: in sweet-bitter flavor, neutral-natured, effective in moistening lung and preventing asthma, killing louse and parasites, used for treating new or chronic cough, whooping cough, phthisis cough;

*Phragmites* stem: in sweet favor, cold-natured, effective in clearing heat and producing saliva, eliminating phlegm, promoting defecation and urination, used for treating cough caused by lung heat, thick phlegm, capable of eliminating phlegm and preventing asthma;

*Bulbus Fritillariae Cirrhosae*: in sweet-bitter favor, lightly cold-natured, effective in eliminating phlegm and relieving cough, clearing heat, removing masses, used for treating deficiency syndrome of the lung, chronic cough, phlegm shortage, dry throat, yellow viscous expectoration, capable of eliminating phlegm, relieving cough and preventing asthma;

*Flos Farfarae*: effective in moistening lung, descending qi, breaking blockage, eliminating turbid phlegm, relieving cough, used for treating new or chronic cough, asthma, hemoptysis;

*Exocarpium Citri Rubrum*: effective in dispelling cold, eliminating dampness, regulating qi-flowing for eliminating phlegm, used for treating wind-cold cough, excessive phlegm, converse qi;

Radix *Peucedani*: in pungent-bitter favor, lightly cold-natured, effective in expelling wind-heat, directing qi downward, eliminating phlegm, used for treating mixture of exopathic cold and heat, lung heat, phlegm blockage, cough with excessive phlegm.

Synergistic effect could be achieved by cooperation of above components, and the effect would be improved.

Embodiment 1

Ingredients by weight: 15 parts of *Perilla* Leaf, 15 parts of Periostracum Cicada, and 15 parts of *lumbricus*; The oral liquid is a concentrated decotion.

Embodiment 2

Ingredients by weight: 15 parts of *Perilla* Leaf, 10 parts of Periostracum cicada, 15 parts of *lumbricus*, 8 parts of Radix *Peucedani*, 8 parts of Radix *Stemonae*, 15 parts of *phragmites* stem, 20 parts of *Flos Farfarae*, 20 parts of *Bulbus Fritillariae Cirrhosae*, and 15 parts of *Exocarpium Citri Rubrum*; The oral liquid is a concentrated decotion.

Embodiment 3

Ingredients by weight: 25 parts of *Perilla* Leaf, 20 parts of periostracum cicada, 20 parts of *lumbricus*, 15 parts of Radix *Peucedani*, 15 parts of Radix *Stemonae*, 8 parts of *phragmites* stem, 18 parts of *Flos Farfarae*, 25 parts of *Bulbus Fritillariae Cirrhosae*, and 10 parts of *Exocarpium Citri rubrum*; The oral liquid is a concentrated decotion.

Embodiment 4

Ingredient by weight: 15 parts of *Perilla* Leaf, 15 parts of Periostracum Cicada, 15 parts of *lumbricus*, 15 parts of Radix *Peucedani*, 15 parts of Radix *Stemonae*, 15 parts of *phragmites* stem, 15 parts of *Flos Farfarae*, 15 parts of *Bulbus Fritillariae Cirrhosae*, and 15 parts of *Exocarpium Citri Rubrum*; The oral liquid is a concentrated decotion.

Control Experiment

Experimental animals: Kunming mice, 18-22 g body weight; Guinea pigs, 250-300 g body weight. The experiments are divided into treatment group, control group, and model group. In the treatment group, the oral liquid for treating allergic cough (anemogenous cough) is taken through intragastric administration. In the control group, control drugs are taken through intragastric administration. In the model group, normal saline is taken through intragastric administration to act as a blank control.

Experimental methods and results are as follows:
1. ammonia water inducing cough in mice: 10 mice in each group; In the treatment group, the oral liquid for treating allergic cough (anemogenous cough) of Embodiment 4 according to the present invention is taken through intragastric administration; In the control group, expectorant is taken through intragastric administration; In the model group, an equal volume of normal saline is taken through intragastric administration. Apply ammonia water spray with constant pressure to mice after 30 minutes, observe and record the times of cough within 3 minutes. The results has shown that the cough inhibition rate after taking the oral liquid for treating allergic cough (anemogenous cough) of the present invention is 80%, better than 63.7% of the control group, which indicates that the oral liquid for treating allergic cough (anemogenous cough) of the present invention is capable of decreasing times of cough of the mice due to stimulus caused by ammonia water, and it is effective in relieving cough.
2. Phenol red apophlegmating in mice: 20 mice in each group; In the treatment group, the oral liquid for treating allergic cough (anemogenous cough) of Embodiment 4 according to the present invention is taken through intragastric administration; In the control group, expectorant is taken through intragastric administration; In the model group, an equal volume of normal saline of is taken through intragastric administration. Inject 5% Phenol red solution into enterocoelia of the mice after 30 minutes, and the mice died of suffocation after 30 minutes. Cut the tracheas between thyroid cartilages and tracheal bifurcations, and immerse them in normal saline and add sodium bicarbonate. Take suitable amount of solution to measure optical density, and the amount of phenol red is determinated by comparing with stand curve of phenol red. It is found that the output of phenol red is increased by 290% after taking the oral liquid for treating allergic cough (anemogenous cough), which is better than 257.8% in the control group. The result shows that the oral liquid for treating allergic cough (anemogenous cough) is capable of promoting mucus secretion, leading to low viscosity of phlegm and easy expectoration, and it is more effective in eliminating phlegm comparing with drugs in the prior art.
3. Trachea spasm in guinea pigs: 6 guinea pigs in each group; In the treatment group, the oral liquid for treating allergic cough (anemogenous cough) of Embodiment 1 according to the present invention is taken through intragastric administration; In the control group, aminophyline is taken through intragastric administration; In the model group, an equal volume of normal saline is taken through intragastric administration. Mixed spray of 2% acetyl choline and 0.4% histamine with constant pressure is applied to guinea pigs after 30 minutes, observe and record the number of animals who convulsed and fell over within 6 minutes and the average latency time for spasm. It is found that only one guinea pig was convulsed and fell over after taking the oral liquid for treating allergic cough (anemogenous cough), the latency time is prolonged as same as in the control group, and latency time of two groups are close. It is shown that it is obviously facilitate relieving spasm of smooth muscle of trachea and eliminating phlegm.
4. Mice ear swelling: 10 mice in each group; In the treatment group, the oral liquid for treating allergic cough (anemogenous cough) of Embodiment 4 according to the present invention is taken through intragastric administration; In the control group, aspirin is taken through intragastric administration; In the model group, an equal volume of normal saline is taken through intragastric administration. Apply xylene solution on both sides of left ear of mice after 15 minutes, and apply the control group on the right ear. Take ears with a diameter of 7.55 mm and weight them after 2 hours, the difference value between the left ear and the right ear is defined as an ear swelling degree. The difference value between the left ear and the right ear in the treatment group is close to that in the control group, which shows the oral liquid for treating allergic cough (anemogenous cough) of the present invention is obviously effective in anti-inflammation.

Conclusion: comparing with drugs for treating allergic cough in the prior art, the oral liquid of the present invention is advantageous in anti-inflammation, eliminating wind and expelling cold, dispersing wind and expelling heat, relieving cough, preventing asthma, whereby having better effect. The effect in application of clinical treatment is also prominent.

What is claimed is:
1. A capsule or tablet consisting essentially of *perilla* leaf extract, periostracum cicada extract, *lumbricus* and *Flos Farfarae* extract.
2. A capsule or tablet consisting essentially of *perilla* leaf extract, periostracum cicada extract, *lumbricus* and *Flos Farfarae* extract and a component selected from the group con- sisting of Radix *Peucedani*, Radix *Stemonae*, *phragmites* stem, *Bulbus Fritillariae Cirrhosae, Exocarpium Citri Rubrum* and mixtures thereof.

3. The capsule or tablet of claim 1 which is 5 to 25 parts by weight of *Perilla* Leaf, 5 to 25 parts by weight of Periostracum Cicada, 5 to 25 parts by weight of *lumbricus*, and 5 to 25 parts by weight of *Flos Farfarae*.

4. The capsule or tablet of claim 2, wherein said component is at least one of 5 to 25 parts by weight of Radix *Peucedani*, 5 to 25 parts by weight of Radix *Stemonae*, 5 to 25 parts by weight of *phragmites* stem, 5 to 25 parts by weight of *Bulbus Fritillariae Cirrhosae*, and 5 to 25 parts by weight of *Exocarpium Citri Rubrum*.

5. A capsule or tablet of consisting essentially of 10 to 20 parts by weight of *Perilla* Leaf, 10 to 20 parts by weight of Periostracum Cicada, 10 to 20 parts by weight of *lumbricus*, and 10 to 20 parts by weight of *Flos Farfarae*, 10 to 20 parts by weight of Radix *Peucedani*, 10 to 20 parts by weight of Radix *Stemonae*, 10 to 20 parts by weight of *phragmites* stem, 10 to 20 parts by weight of *Bulbus Fritillariae Cirrhosae*, and 10 to 20 parts by weight of *Exocarpium Citri Rubrum*.

\* \* \* \* \*